United States Patent
Lotterhos et al.

(10) Patent No.: US 9,579,681 B2
(45) Date of Patent: Feb. 28, 2017

(54) APPARATUS AND METHOD OF APPLYING SUNSCREEN OR SIMILAR LIQUID

(76) Inventors: William Christopher Lotterhos, Spring Hill, TN (US); Richard N. Linder, Jr., Collierville, TN (US)

( * ) Notice: Subject to any disclaimer, the term of this patent is extended or adjusted under 35 U.S.C. 154(b) by 698 days.

(21) Appl. No.: 12/252,337

(22) Filed: Oct. 15, 2008

(65) Prior Publication Data
US 2009/0157015 A1    Jun. 18, 2009

Related U.S. Application Data

(63) Continuation-in-part of application No. 11/273,882, filed on Nov. 15, 2005, now Pat. No. 8,069,812.

(60) Provisional application No. 60/664,998, filed on Mar. 24, 2005, provisional application No. 60/980,155, filed on Oct. 15, 2007, provisional application No. 60/980,156, filed on Oct. 15, 2007.

(51) Int. Cl.
| | |
|---|---|
| *B05B 3/00* | (2006.01) |
| *B05B 12/02* | (2006.01) |
| *B05B 15/12* | (2006.01) |
| *G07F 13/08* | (2006.01) |
| *G07F 13/00* | (2006.01) |

(52) U.S. Cl.
CPC ............... *B05B 15/12* (2013.01); *G07F 13/00* (2013.01); *G07F 13/08* (2013.01); *A45D 2200/057* (2013.01); *B05B 12/02* (2013.01); *B05B 15/1222* (2013.01)

(58) Field of Classification Search
USPC .. 118/326, 309, DIG. 7, 300, 323, 663, 668, 118/669, 679–682; 4/525, 597, 612, 614, 4/603; 604/289–291; 424/78.02, 78.03; 132/333, 320; 119/671
See application file for complete search history.

(56) References Cited

U.S. PATENT DOCUMENTS

| | | | | |
|---|---|---|---|---|
| 716,096 A | * | 12/1902 | Pierce | 4/617 |
| 2,567,506 A | * | 9/1951 | Bowman | A47K 3/284 |
| | | | | 4/598 |
| 4,099,272 A | * | 7/1978 | Sowder | 4/555 |
| 4,303,201 A | * | 12/1981 | Elkins | B05B 1/1636 |
| | | | | 239/381 |
| 4,383,252 A | * | 5/1983 | Purcell et al. | 340/606 |
| 4,430,074 A | * | 2/1984 | Mooring | 604/506 |
| 4,441,143 A | * | 4/1984 | Richardson, Jr. | 362/183 |
| 6,711,758 B1 | * | 3/2004 | Terek et al. | 4/620 |

(Continued)

FOREIGN PATENT DOCUMENTS

JP    2005251187 A  *  9/2005  .............  G07F 17/18

*Primary Examiner* — Yewebdar Tadesse
(74) *Attorney, Agent, or Firm* — The Ronald Law Group, LLC

(57) ABSTRACT

A central body or device adapted to take payment in a variety of means and dispense sunscreen, insect repellant, hand sanitizers, or similar lotions, gels, or liquids. The sunscreen (or similar lotion, gel or liquid) may be dispensed in foil packets, plastic bladders, gel packs, or similar containers, or may be dispensed directly, such as through a spray attachment. The device may be unpowered, or powered by a battery, solar panel, or electrical power supply. The device may accept payment in a variety of forms: coins, bills, credit or debit cards, a hotel or resort access or room card, or the like. It may be mounted on a wall or vertical flat surface, or mounted on a pole or stand.

12 Claims, 6 Drawing Sheets

(56) References Cited

U.S. PATENT DOCUMENTS

| | | | | |
|---|---|---|---|---|
| 6,918,897 B2* | 7/2005 | Severino | ............... | 604/289 |
| 2006/0037532 A1* | 2/2006 | Eidson | ............... | 118/31.5 |
| 2006/0231567 A1* | 10/2006 | Perrone | ............... | 222/2 |
| 2006/0265246 A1* | 11/2006 | Hoag | ............... | 705/2 |
| 2007/0045449 A1* | 3/2007 | Herring et al. | ............... | 239/525 |
| 2007/0125798 A1* | 6/2007 | McGuire | ............... | 222/14 |
| 2009/0031492 A1* | 2/2009 | Foutz et al. | ............... | 4/597 |

* cited by examiner

APPARATUS AND METHOD OF APPLYING SUNSCREEN OR SIMILAR LIQUID

This application is a continuation-in-part of U.S. application Ser. No. 11/273,882, filed Nov. 15, 2005, now U.S. Pat. No. 8,069,812 by William Christopher Lotterhos and Richard Linder, and claims priority to and the benefit of that application, and U.S. Provisional Application No. 60/664,998, filed Mar. 24, 2005, Application No. 60/980,155, filed Oct. 15, 2007, and Application No. 60/980,156, filed Oct. 15, 2007, and is entitled in whole or in part to those filing dates for priority. The specifications and accompanying documents of U.S. Provisional Patent Application Nos. 60/664,998, 60/980,155, and 60/980,156, and U.S. application Ser. No. 11/273,882, are incorporated herein in their entireties by reference.

FIELD OF INVENTION

This invention relates generally to an apparatus and method for applying sunscreen, insect repellent, aloe lotion, skin care products, or similar liquids or lotions, and more particularly to a portable apparatus for the spray application of sunscreen, insect repellent, aloe lotion, skin care products, or similar liquids or lotions.

BACKGROUND OF INVENTION

The importance of the proper application and use of sunscreen by individuals whose skin may be exposed to the sun, especially for extended periods of time, is well known. Failure to use sunscreen, or improperly using or applying sunscreen, can lead to a number of undesired consequences, including sunburns, rashes, or skin cancer.

Most sunscreen and similar lotions or products typically come packaged for direct application by an individual from the bottle or package. Proper application of standard sunscreens usually requires application to the skin area to be protected at or close to the time of exposure to the sun. Problems frequently arise when individuals forget to bring sunscreen with them and reach the location, such as a beach, pool, or water park, where they will be exposed. Many individuals at this point simply decide to go without protection rather than take the time to retrieve the sunscreen or buy a replacement.

A similar problem arises from the choice of different levels of protection and similar features that are available in sunscreens (e.g., 15 SPF, 30 SPF, 50 SPF, waterproof). An individual may not know what particular product should be used at a particular location until that location is reached. Moreover, protection needs may vary over time, so that a sunscreen that is appropriate at one time may not be appropriate several hours later. Few individuals are willing to take several sunscreen products with them to address these needs.

Additional problems may arise based on the location where the sunscreen is to be applied. At a beach or other location with sand, for example, the sunscreen often picks up sand or other particles, thus rubbing or irritating the skin, and perhaps leading to an incomplete application of sunscreen. Furthermore, an individual may have difficulty applying sunscreen to all parts of his or her body that will be exposed, leading to areas where the sunscreen is unevenly applied or even absent. Similarly, after exposure to the sun, the application of aloe lotion or a similar liquid to exposed skin may be called for, and the problems described above may arise.

Similar problems arise with the application of insect or mosquito repellent. Failure to bring the product or improper or incomplete application commonly lead to insect bites, which can cause irritation, discomfort, or disease.

Accordingly, what is needed is an apparatus and method for applying sunscreen, insect repellent, aloe lotion, or similar liquids to substantial portions of the human body, including the entire area expected to be exposed to sunlight, similar radiation, or the air, with a variety of types of sunscreen, repellents, lotions or liquids in a quick and convenient manner.

SUMMARY OF THE INVENTION

In one exemplary embodiment, the present invention provides for a booth with a plurality of spray nozzles for the application of sunscreen, insect repellent, aloe lotion, skin care products, or similar lotions or liquids to substantial portions of the human body. Spray nozzles are oriented to avoid opposing air or spray flows that may cause inefficient or uneven application of the lotion or liquid. In one exemplary embodiment, spray nozzles may be adjustable by the user or others. In another exemplary embodiment, the invention includes means for rinsing the body prior to application of the lotion or liquid to promote even and unobstructed application to the body. In another exemplary embodiment, means for washing down the booth between or after use is provided. Power may be provided by electrical power sources, a battery, or solar panel(s).

In another embodiment, the present invention comprises a cabinet with one or more doors that open. The interior of the cabinet comprises a system for spraying sunscreen from a plurality of nozzles located on the front of the cabinet, said nozzles positioned to spray sunscreen, insect repellent, or similar liquid, on all or substantially all of a person standing in front of the cabinet. The spray system may be powered by a solar panel, an electrical cord, batteries, or some other means for supplying power. A solar panel may be used in conjunction with a battery for storing energy generated by the solar panel. The power system further may comprise a solar regulator.

In yet another embodiment, the present invention comprises a vending machine body or device adapted to take payment in a variety of means and dispense sunscreen, insect repellant, hand sanitizers, or similar lotions, gels, or liquids. The sunscreen (or similar lotion, gel or liquid) may be dispensed in foil packets, plastic bladders, gel packs, or similar containers. In another embodiment, the sunscreen (or similar lotion, gel or liquid) may be dispensed directly. In one embodiment, a spray attachment may be attached to the vending machine body to spray the liquid onto the user's hands, body part(s), or other area to be covered or treated.

Still other advantages of various embodiments will become apparent to those skilled in this art from the following description wherein there are shown and described exemplary embodiments of this invention simply for the purposes of illustration. As will be realized, the invention is capable of other different aspects and embodiments without departing from the scope of the invention. Accordingly, the advantages, drawings, and descriptions are illustrative in nature and not restrictive in nature.

DETAILED DESCRIPTION OF THE INVENTION

Figure 1:
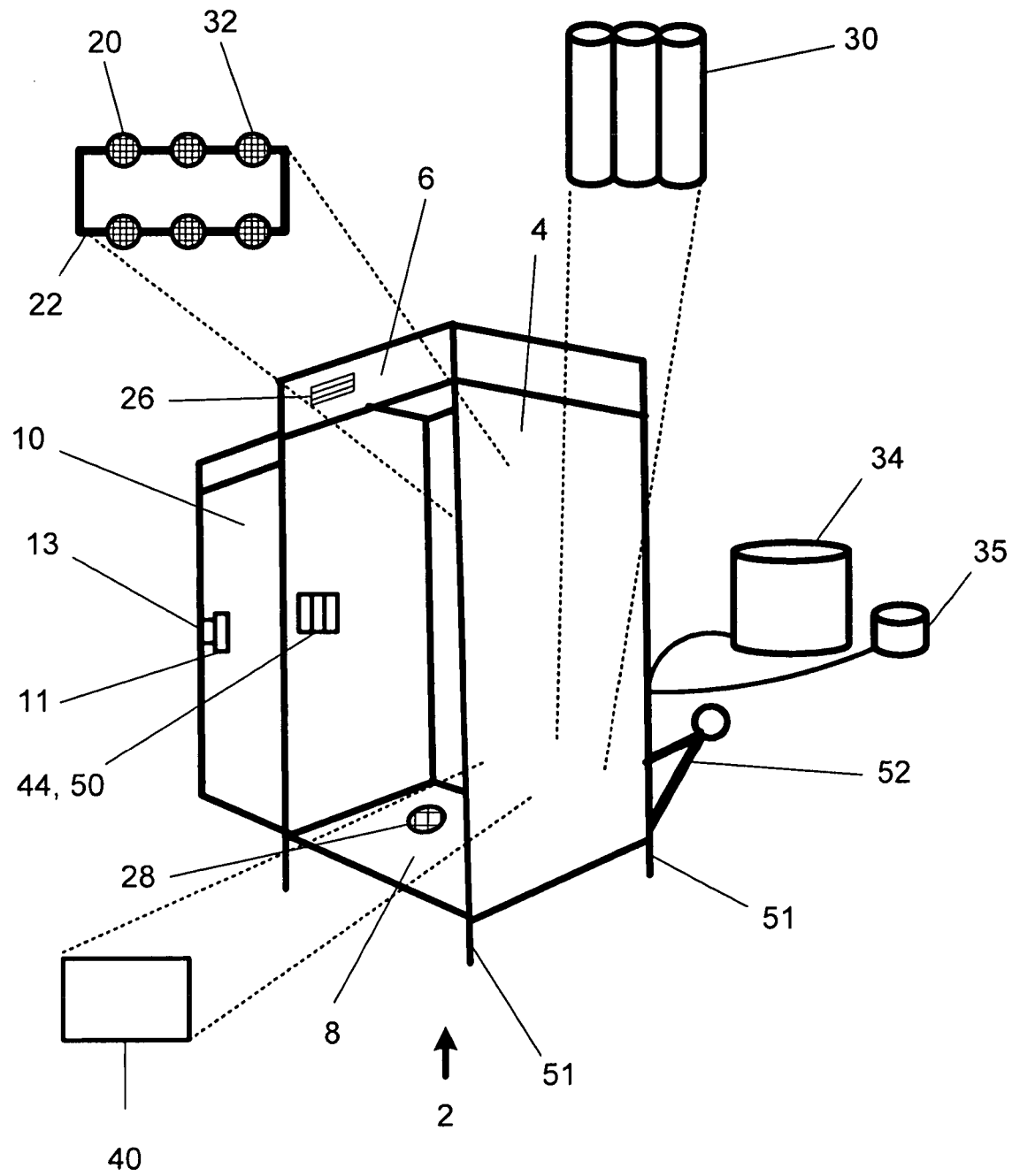
FIG. 1 shows a perspective view of one embodiment of the present invention.

Referring now to the figures, wherein like references identify like elements of the invention, FIG. 1 illustrates an exemplary embodiment of a sunscreen application booth in accordance with the present invention. A booth 2 comprises one or more walls 4, and a floor 8. The booth 2 may also comprise a top 6. One or more doors 10 are used for access to the interior of the booth 2. A door 10 may be a portion of a wall 4 or may be an entire wall itself. One or more of the walls may be opaque, translucent, or transparent. In one exemplary embodiment, the walls are all opaque, or all transparent or translucent. The number and configuration of walls may vary, as the booth 2 may be circular, conical, triangular, rectangular, square or some other shape. The walls, floor and top may be made of any suitable material, including acrylic, other forms of plastic or plastic-like material, glass, or metal. A mat or anti-slipping flooring system 8a, such as Safety Lok-Tyle Mats, may be placed on the floor 8 or integrated as part of the floor.

A plurality of spray nozzles 20 or other means for spraying a sunscreen or similar liquid or lotion are located in the interior of the booth 2. The spray nozzles 20 may be integral with the walls 4, top 6, or floor 8, or may be mounted thereon. In one exemplary embodiment, the spray nozzles 20 are mounted on one or more bars 22, which in turn are mounted on the interior portions of the booth. The spray nozzles 20 may be placed in a variety of configurations. The spray nozzles 20 may be fixed in place, or some or all may be adjustable. One or more nozzles may also have sensors, such as infrared sensors, built-in or attached so as to indicate when a person is within a certain distance in front of the nozzle. This can be used to control operation of the nozzle.

Figure 2:
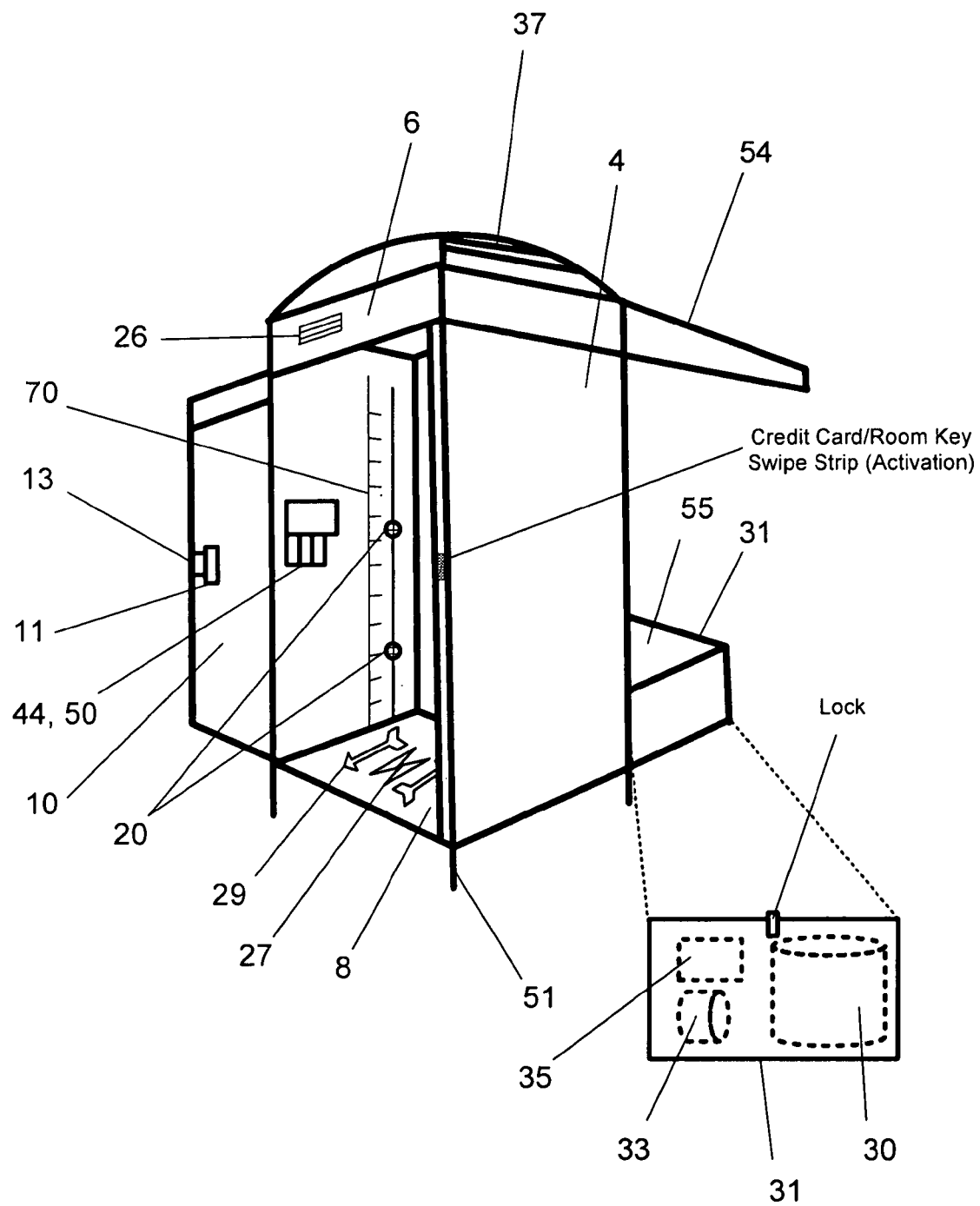
FIG. 2 shows a perspective view of another embodiment of the present invention.

In one exemplary embodiment, as seen in FIG. 2, two spray nozzles 20 are located on the interior of the booth 2 in one corner 10. The lower of the nozzles is positioned to spray the sunscreen or similar liquid or lotion on the lower half of the user, while the upper nozzle is positioned to spray the upper half of the user (which can include the head, but also may be limited to going no higher than the neck). The user turns himself or herself in place for coverage of all sides. One or both of the two spray nozzles 20 may be adjustable. In another exemplary embodiment, the bottom nozzle is fixed, while the top nozzle may be moved vertically along a shaft or bar to an appropriate height for the particular user. Markings 70 may be used to guide the user in adjusting the height of the nozzle. While the booth 2 may be of various sizes and configurations, minimum and maximum height restrictions may be applied. Thus, for example, in one embodiment the interior of the booth 2 may be 6 feet 10 inches in height and able to accommodate users up to 6 feet 5 inches in height.

Figure 3:
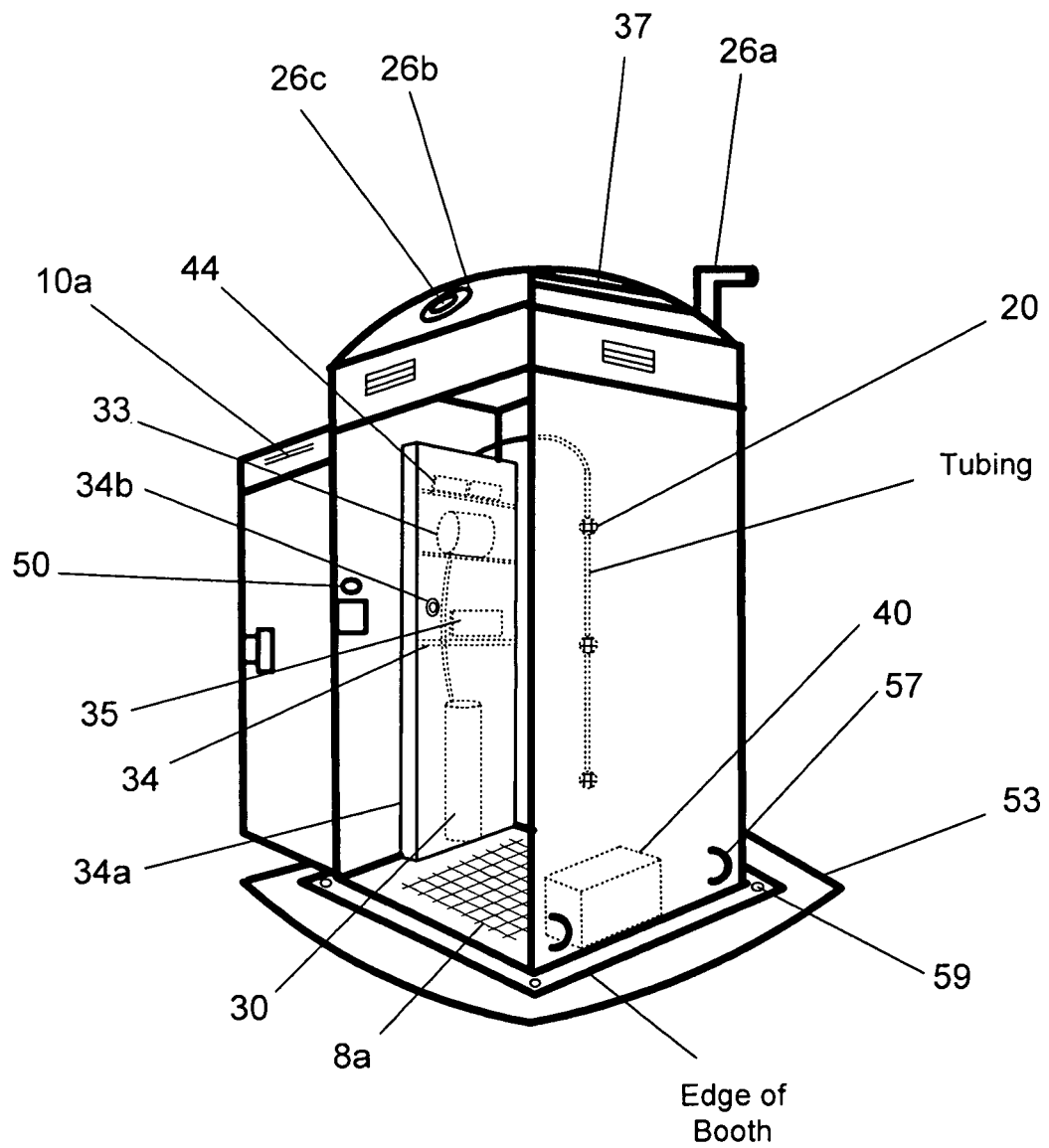
FIG. 3 shows a perspective view of yet another embodiment of the present invention.

In another exemplary embodiment, as seen in FIG. 3, three spray nozzles 20 may be located on the interior of the booth 2. The upper and lower nozzles would provide coverage as described above, while a middle nozzle would cover the middle of the user.

One or more air vents 26 may be located in the wall 4 or top 6 to provide air circulation. In one exemplary embodiment, an air vent 26 is located at the top of one or more of the walls 4 or in the top 6. In another exemplary embodiment, as shown in FIG. 3, one vent may comprise a fresh air intake vent or cowl 26a and an exit vent 26b. The exit vent 26b may have means of drawing air out of the interior booth 2, such as a fan or pump 26c, which may be powered in a variety of means, including by electricity, battery, or solar power.

One or more drains 28 may be located in the floor 8 or in the bottom section of one or more of the walls 4. A drain 28 may be connected to means for disposing of the sunscreen, water, or other liquids running into the drain. If the sunscreen or liquid or lotion being sprayed does not form run-off, condensate, or otherwise collect or pool on the floor or walls, then a drain may not be needed. This depends on the formulation of what is sprayed, the duration of the spraying, and other factors. The duration of the spraying can be of any length, depending on the sunscreen or liquid or lotion being sprayed and the circumstances of the spraying. In one exemplary embodiment, a two-nozzle or three-nozzle system as shown in FIGS. 2 and 3 may completely cover an individual with a spray duration in the range of 5 to 15 seconds.

The floor may be marked with footprints 27 to show the user where to stand during operation. For configurations where the user must turn in place in front of the nozzles to obtain complete coverage, the floor may also be marked with arrows, additional footprints, or similar markings or directions 29 to show the user where to stand and how to move during operation.

The spray nozzles 20 are connected to one or more storage tanks 30 containing sunscreen or similar lotions or liquids. In one exemplary embodiment, each storage tank 30 contains a sunscreen of different protective levels or properties (e.g., different SPF values, waterproof vs. non-waterproof). During normal operation of the booth 2, the sunscreen from the appropriate storage tank 30 is sprayed through the spray nozzles 20 onto the individual standing inside the booth 2. Storage tanks 30 may be of various sizes and shapes, and may be integrated with the booth (inside or outside) or separate. In one exemplary embodiment, the storage tank or tanks 30 are stored in a box or locker 31 fastened to the outside of the booth 2 (or integrated with the booth 2). The box or locker 31 may be secured or locked to prevent access except by authorized individuals. The box or locker 31 may also contain the compressor or pump 33 or other means for causing the sunscreen, lotion or liquid to be delivered to the nozzles. The box or locker 31 may also contain a battery 35 or means for providing power. The battery 35 may be charged by means of a standard electric plug or similar electric power source, or by a solar panel. In one exemplary embodiment, one or more solar panels 37 may be fastened to the top or sides of the booth 2 to generate electricity and charge the battery 35. In configurations where a battery is absent, power may be provided directly by a standard electric plug, solar panel, or other electric power source.

In an alternative embodiment, as seen in FIG. 3, the storage tank 30, battery 35, compressor or pump 33, and other components may be located inside the booth. As such, these components may stand on the floor, be fastened or affixed to one or more walls, or sit on one or more shelves 34 in an interior cabinet 34*a*. The interior cabinet 34*a* may be provided with a lock 34*b*.

In another exemplary embodiment, a microcontroller or programmable logic controller or similar control device 44 is used to control and monitor operations. The control device 44 may be located inside or outside of the booth. As shown in FIG. 3, the control device or PLC is located inside the interior cabinet 34*a*. The control device, among other functions, controls spray cycles, controls the delay in spray timing, controls the reset cycle, controls the door and/or nozzle sensors, and keeps track of operations data (such as the number of uses).

In another exemplary embodiment, means for rinsing the individual prior to application of the sunscreen is provided. Rinsing means could use the same spray nozzles 20 through which sunscreen is applied, or could comprise a plurality of separate rinse spray nozzles 32 through which the rinsing liquid, such as water, is sprayed. In an alternative embodiment, the rinsing means may include one or more separate hoses (not shown) in the interior or on the exterior of the booth for use by the individual for more specific rinsing needs. The rinsing means is connected to one or more storage tanks 34 containing the rinsing liquid, such as water. The rinsing means may also comprise a cleaning agent, which may be stored in the same storage tanks 34 as the rinsing liquid, or in separate storage means 35. Storage tanks 34, 35 may be of various sizes and shapes, internal and/or external, and may be integrated with the booth or separate.

In yet another exemplary embodiment, means for rinsing the interior of the booth after use or a number of successive uses is provided. The rinsing means would function similarly to the rinsing means described above for rinsing the user prior to application of the sunscreen, and could be the same rinsing means. One or more shower heads also could be provided on the outside of the booth for rinsing by the user.

The door 10 operates by means of a handle 11, and can be opened from either side. In one exemplary embodiment, means for locking the door 13 is provided. During normal use, the user may lock the door from the inside to ensure privacy and safe operation. The booth 2 also may be configured with a door sensor 10*a* or similar device so that the sunscreen application or various rinsing functions may not take place unless the door is closed and/or locked. The lock may also be timed, so as to automatically open after a certain period of time, or to lock and unlock at set times during the day. In another exemplary embodiment, even when the door is locked, the door should be able to be opened from the inside. In yet another exemplary embodiment, the door 10 may only be opened from the outside if the user swipes a credit card, debit card, hotel passkey, or similar device through a card reader. Simple access to the booth may or may not incur a charge. Records of entry time and duration could be maintained, and could be used to resolve issues of vandalism and the like.

A storage box or unit 40 unit may be provided for the user to store clothes, shoes, or valuables while using the booth 2. The storage unit 40 may be located inside or outside the booth, and may be locked if outside. It may be free standing, mounted on the booth 2, or integrated into the booth wall, floor or top. If inside the booth 2, the storage unit 40 ideally would be air or water tight, and could include some sealing means.

In an alternative embodiment, the booth 2 may be air-conditioned or heated to a desired temperature.

In another embodiment, inside or outside the booth is a control unit 50 which accepts payment in a variety of forms (e.g., cash, credit or debit card, or the like). The control unit 50 also provides the user a selection of options, such as the type of sunscreen or liquid to be sprayed, the time or duration of the spraying, and possibly a particular body zone to be sprayed (e.g., leg area, which would cause only the spray nozzles below waist height to operate). The control unit 50 also would provide instructions or help to the user during the entire process. Such instructions could be in writing on a screen or spoken, or both. The control unit 50, or functional parts of the control unit, such as the payment acceptor, may be located outside the booth, in an alternative configuration. The control unit 50 may be in wired or wireless communication with an outside computer or monitor, so that an owner or operator of the booth may monitor the status of the booth 2 remotely, including when the booth is in use, the amount of sunscreen, water, or rinsing liquid remaining, when the booth door is left open for an extended period of time, and the like. Alarms or alerts can be provided when certain conditions are detected, or when service is needed at the booth. The monetary control unit 50 may be used in conjunction with a control device 44 as described above, or the two devices may be combined into a single unit.

Booths 2 may be portable or transportable, or may be placed on a permanent or semi-permanent basis. Means for securing the booth 2 in a particular location may be provided, such as fastening rings or holes 59 through which stakes may be driven, or integral stakes extending down from the bottom of the booth 51. Wheels or skids 53 may be attached to the booth 2 for ease of transport. Similarly, means for towing, such as a hitch 52, may be provided. In one exemplary embodiment, as shown in FIG. 3, a skid 53 may encompass the entire bottom of the booth. Alternatively, such a skid 53 may also serve as part of a drainage system. Handles 57 may be affixed to various parts of the booth to assist in moving the booth.

Maintenance of the booth 2 may be done on a periodic schedule, depending on the nature, type and duration of use. Sensors may be built into the various components to provide an alert when certain conditions indicate that maintenance may be needed, such as the booth door being open for an extended period of time, fluid levels in one or more tanks running low, battery charge running low, loss of power, and so on. A switch on the inside of the booth also may be provided for the user to indicate when maintenance for the booth is needed, said switch providing an alert as above. An infrared sensor may be used to detect the height of the user, and prevent operation if the height is not within acceptable operating standards (e.g., the user must be taller than 42 inches).

An awning or shade 54 may be provided on one or more sides of the booth 2. This would provide shade to users, and may be of a distinctive color, pattern or appearance so as to catch the eye and/or identify the booth 2 for potential users. Loudspeakers playing music or other sounds also could be used to attract the attention of potential users. Advertisements also could be pasted on the outside or inside of the booth. In one exemplary embodiment, the outside may be covered with a negative heat press for graphics on an acrylic material, which may be fastened on the outside by a variety of means, such as being fit or slid into plastic, metal or aluminum frames. In another embodiment, seating means, such as benches 55, may be provided on one or more sides on the outside of the booth 2. These may be fastened to the booth, integrated with the booth, or separate. Similarly, seating means may be provided inside the booth 2 for the user.

During normal operation of the booth 2, the user enters the booth 2 and closes and locks the door 10. The user then removes excess clothing and places the clothing and anything else to be protected (such as shoes, wallets, sunglasses, towels, or bags) inside the storage unit 40 and closes the storage unit 40 securely. The user then makes payment through the monetary control unit 50, selects the type of sunscreen to be applied, as well as possibly making other choices about the duration or type of spraying service desired (including whether to obtain a pre-application rinse). The user also may don a protective hair covering and/or eye covering, which may be disposable and provided by the control unit 50 or other means when a service is purchased. When the user is ready for the spraying application to begin, the user presses a start button 51 inside the booth (which may be located on or near the control unit 50), and the spraying of the sunscreen begins. The spraying may start immediately, or may be delayed for a short time (e.g., 1 second) to allow the user to prepare. The user may stand still, or may turn or rotate in place, as desired or needed. The user may close his or her eyes and/or mouth during this process. In one exemplary embodiment, the user turns in place for 10 seconds. The sunscreen is applied evenly to all exposed skin in the area selected. After the application process is complete, the user retrieves his or her items from the storage unit 40, and exits the booth 2. The booth may then self-lock and initiate an interior rinsing process.

In one exemplary embodiment, a two ounce application of sunscreen can cover a typical individual when sprayed with a two-nozzle configuration as seen in FIG. 2. A single 500 fluid ounce storage tank thus would contain sufficient fluid for 250 applications (or 250 individuals, assuming one individual per application). Assuming a usage rate of 85 people per day in a beach location, the tank would last approximately 3 days, and thus require maintenance every two to three days.

In another exemplary embodiment, as seen in FIG. 3, the booth may be a square on the outside, 62 inches long on each side, and 94 inches high (including the solar panel). In this configuration, the booth may weigh only approximately 280 pounds.

In another exemplary embodiment, the nozzles 20 are engineered for precision atomization, and may include mesh screens.

Figure 4:
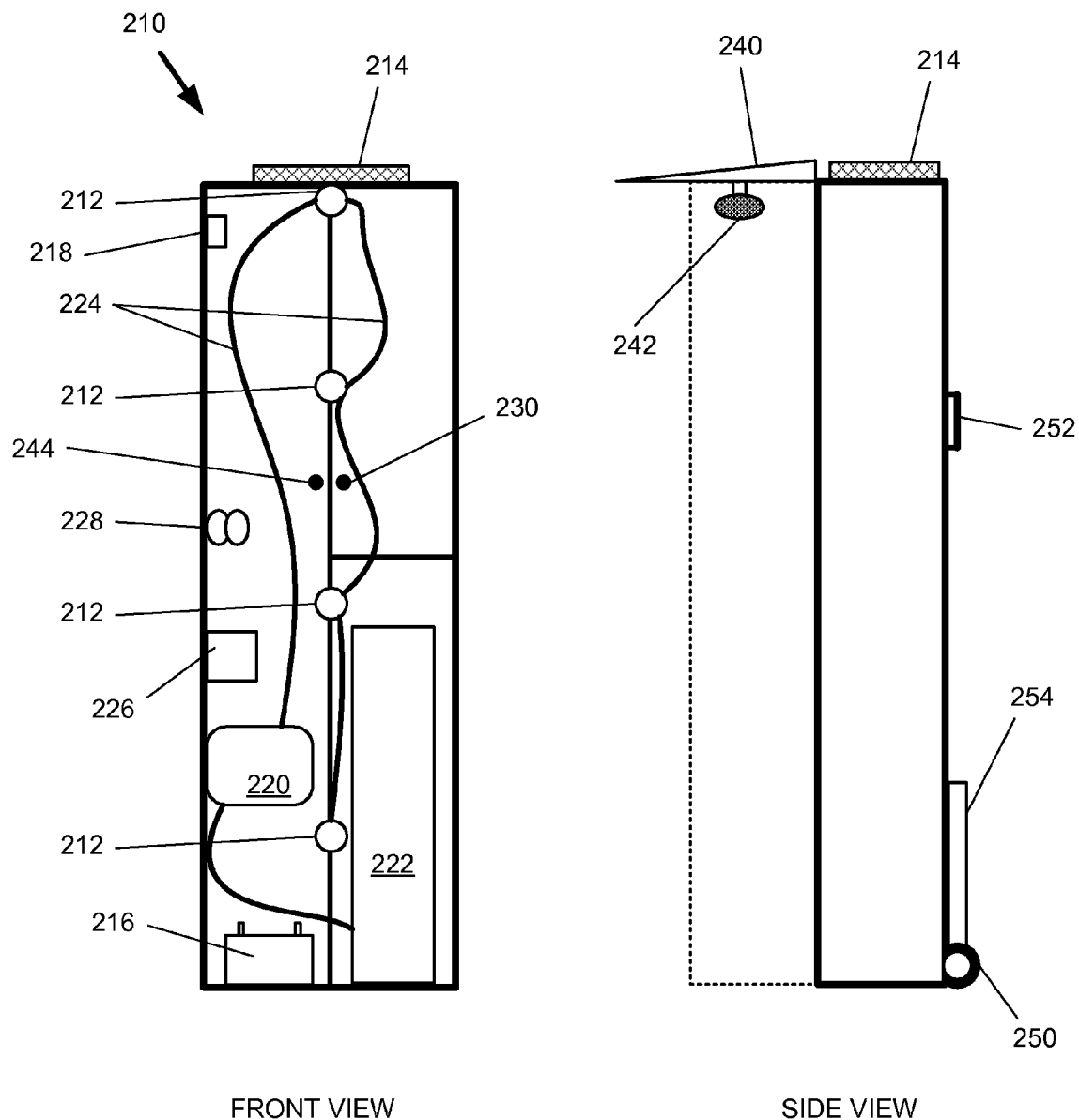
FIG. 4 shows front and side views of a portable device in accordance with one embodiment of the present invention.

In yet another exemplary embodiment, as shown in FIG. 4, the present invention comprises a cabinet 210 with one or more doors that open. The interior of the cabinet comprises a system for spraying sunscreen from a plurality of nozzles 212 located on the front of the cabinet, said nozzles positioned to spray sunscreen, insect repellent, or similar liquid, on all or substantially all of a person standing in front of the cabinet. The spray system may be powered by a solar panel 214, an electrical cord, batteries 216, or some other means for supplying power. A solar panel may be used in conjunction with a battery for storing energy generated by the solar panel. The power system further comprises a solar regulator 218.

The spray system comprises a compressor 220, a tank 222 for storing sunscreen lotion or insect repellent, tubing 224 for transporting the sunscreen or insect repellent under pressure from the compressor to the nozzles 212. The system further comprises a programmable logic controller (PLC) 226, and solenoids 228. One or more storage shelves may be provided in the cabinet. In one exemplary embodiment, the tank can contain 3 to 5 gallons of sunscreen.

The user initiates the spraying of the sunscreen by pressing a start button 230. The start button may be positioned on the front of the cabinet, or some other position convenient to the user. The system then sprays sunscreen through the nozzles. In one exemplary embodiment, the system sprays for a set period of time. Alternatively, the system may spray for as long as the start button is depressed.

In yet another embodiment, the invention comprises a canopy or awning 240 extending over some or all of the top of the cabinet and over the front and/or sides. In one exemplary embodiment, the canopy extends for 20 to 24 inches over the front of the cabinet. A shower head 242 may be located on the underside of the canopy so as to enable a person standing in front of the cabinet to shower with water. Water may be supplied from a tank in the cabinet, or from a hose that is connected to the shower system. The shower may be triggered with the start button 230, or by a separate shower switch 244. The connector may be a standard hose connector, and may be located in the back of the cabinet.

In one embodiment, the cabinet has wheels 250 and a handle 252 to enable the cabinet to be tilted and moved easily. An ice chest 254 also may be placed on the outside of the cabinet. In one exemplary embodiment, the ice chest 254 is located on the lower back of the cabinet, between or just above the wheels 250. In one embodiment, where the wheels are located 30 inches apart, the ice chest is up to 28 inches wide, 15 inches deep, and may extend for 28 to 30 inches up the back. The ice chest may be stainless steel, or some material to match the décor of the cabinet.

In one exemplary embodiment, the cabinet is approximately 7 feet tall, 33 inches wide, and 10 inches deep, and weighs from 75 to 150 pounds.

Other attachments or accessories include speakers for playing music (such as from an IPOD or CD player), a built-in radio or CD player or MP3 music player (or similar device), an antibacterial floor mat (to be placed in the front of the cabinet), a plug-in adapter, and/or an air fitting (from the compressor, to blow up rafts and other inflatables).

The cabinet may be made of any suitable material, and may be either water-resistant or water-repellant, or treated to be such. The outside of the cabinet may be provided with a variety of looks and appearances to suit any particular style (e.g., wooden with black metal hinges; stucco; brick-look; granite; etc.).

Figure 5:
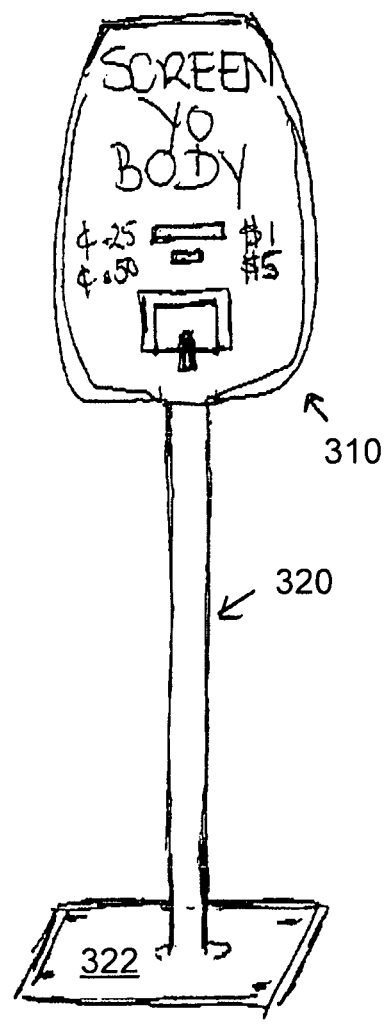
FIG. 5 shows a front view of a vending device in accordance with one embodiment of the present invention.
Figure 6:
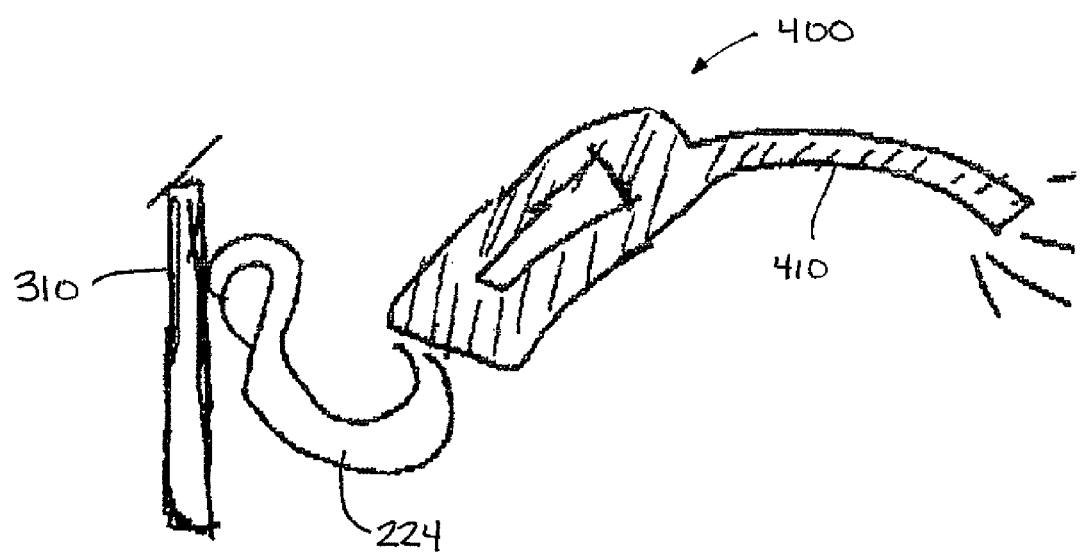
FIG. 6 shows a detailed view of a spray attachment in accordance with another exemplary embodiment of the present invention.

In yet a further exemplary embodiment, as shown in FIG. 5, the present invention comprises a device with a central body, similar to a vending machine body, 310 adapted to take payment in a variety of means and dispense sunscreen, insect repellant, hand sanitizers, or similar lotions, gels, or liquids. The sunscreen (or similar lotion, gel or liquid) may be dispensed in foil packets, plastic bladders, gel packs, or similar containers. In another alternative embodiment, the sunscreen (or similar lotion, gel or liquid) may be dispensed directly. In one embodiment, a spray attachment 400 (as shown in FIG. 6) may be attached to the central body 310 to spray the liquid onto the user's hands, body part(s), or other area to be covered or treated. As further illustrated in FIG. 6, tubing 224, having a proximal end and a distal end, is connected to the central body 310 at the proximal end. A spray attachment head 410 is disposed on the distal end of the tubing.

In one embodiment, the invention is powered by a battery and/or solar panel. The device may be connected to an electrical power supply as well. Alternatively, an unpowered version may be used.

The invention may accept payment in a variety of forms: coins, bills, credit or debit cards, a hotel or resort access or room card, or the like.

The body 310 may be mounted on a wall or similar flat surface. Alternatively, as shown in FIG. 1, the body 310 may be mounted on a pole or stand 320. The pole or stand may be connected to a base 322. The pole or stand (or base) may be affixed or bolted to the ground in any of various ways known in the art. The device may also be free-standing.

In one exemplary embodiment, the invention is weatherproof, with appropriate sealing. The device may be made of any appropriate material, such as metal, heavy-duty plastic, ceramic, or the like. In one embodiment, powder-coated metal may be used. Space may be provided on the invention for a logo, advertising, and the like.

Thus, it should be understood that the embodiments and examples have been chosen and described in order to best illustrate the principals of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art. Accordingly, it is intended that the scope of the invention be defined by the claims appended hereto.

We claim:

1. A device for selectively topically applying a predetermined amount of atomized sunscreen to a person's skin comprising:
   a support pole having an upper end and a lower end;
   a central body, disposed on the upper end of the support pole, comprising a plurality of storage tanks, each storage tank containing a stored supply of sunscreen;
   a spray attachment head having a nozzle configured for atomizing the sunscreen or similar liquid or solution as it is dispensed from the spray attachment head, the spray attachment head attached to the central body by a length of tubing and in fluid communication with the stored supply through the tubing, wherein the spray attachment head can be moved independently of the central body whereby atomized sunscreen or similar liquid or solution can be selectively applied to the person's skin;
   a controller for determining when the amount of sunscreen should be dispensed and a power supply, wherein the stored supply of sunscreen in each storage tank having different characteristics than the other storage tanks.

2. The device of claim 1, wherein the power supply comprises a battery.

3. The device of claim 1, wherein the power supply comprises a solar power device.

4. The device of claim 1, wherein the lower end of the support pole is affixed to a base, the base being removably affixed to the ground.

5. The device of claim 4, wherein the base is attached to the ground or floor.

6. The device of claim 1, wherein the controller further comprises a control device that monitors the number of uses and generates an alert when the stored supply of sunscreen runs low.

7. The device of claim 6, wherein the alert is delivered wirelessly.

8. The device of claim 1, wherein the controller further comprises a control unit of receiving payment.

9. The device of claim 1, wherein the controller further comprises a control unit of monitoring usage time whereby the time that an event of vandalism occurred can be identified.

10. The device of claim 1, wherein the controller further comprises a selector for causing a selected sunscreen to be delivered in response to user choice.

11. The device of claim 1, wherein the support pole is freestanding.

12. The device of claim 1, wherein the nozzle has a mesh screen to assist with atomization of the sunscreen.

\* \* \* \* \*